United States Patent
Mishra et al.

(10) Patent No.: US 6,812,011 B2
(45) Date of Patent: Nov. 2, 2004

(54) PROCESS FOR THE REMOVAL OF CALCIUM IONS FROM THE BRINE BY MARINE CYANOBACTERIA

(75) Inventors: Sandhya Mishra, Gujarat (IN); Pushpito Kumar Ghosh, Gujarat (IN); Mahesh Ramniklal Gandhi, Gujarat (IN); Ajoykumar Murlidhar Bhatt, Gujarat (IN); Shantibhai Amritlal Chauhan, Gujarat (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/777,664

(22) Filed: Feb. 7, 2001

(65) Prior Publication Data

US 2002/0146811 A1 Oct. 10, 2002

(51) Int. Cl.⁷ .............. C12N 1/18; C12P 3/00
(52) U.S. Cl. ........ 435/168; 435/257.1; 435/256.8; 435/262; 435/170; 210/601
(58) Field of Search .......... 435/262, 257.1, 435/170, 256.8, 168; 210/601

(56) References Cited

U.S. PATENT DOCUMENTS 3,396,104 A * 8/1968 Miller ............ 210/54

OTHER PUBLICATIONS

Pillai, V. K., Proc. Natl. Inst. Sci. India, (1955) vol. 21, No. 2, pp. 90–102.*
Heath, et al., J. Appl. Phycol. (1995), Volume Date 1995, 7(4), 367–80.*

* cited by examiner

Primary Examiner—Irene Marx
(74) Attorney, Agent, or Firm—Wenderoth, Lind & Ponack, L.L.P.

(57) ABSTRACT

This invention relates to new use of marine cyanobacteria *lyngbya, Oscillatoria, Sprulina, Anabaena* and *Synechocystis* deposited with ATCC having accession numbers ATCC PTA-4602 and 4603 for the removal of calcium ions from sea-brine and sub-soil brine having a density range 10 to 25.5° Be', by culturing the cyanobacteria, inoculating the cyanobacteria culture to raw brine of 10 to 25.5° Be', filtering the resultant mixture to obtain a brine having less calcium, and to separate the cyanobacteria which can be reused if desired.

18 Claims, 1 Drawing Sheet

PROCESS FOR THE REMOVAL OF CALCIUM IONS FROM THE BRINE BY MARINE CYANOBACTERIA

FIELD OF THE INVENTION

Figure 1:
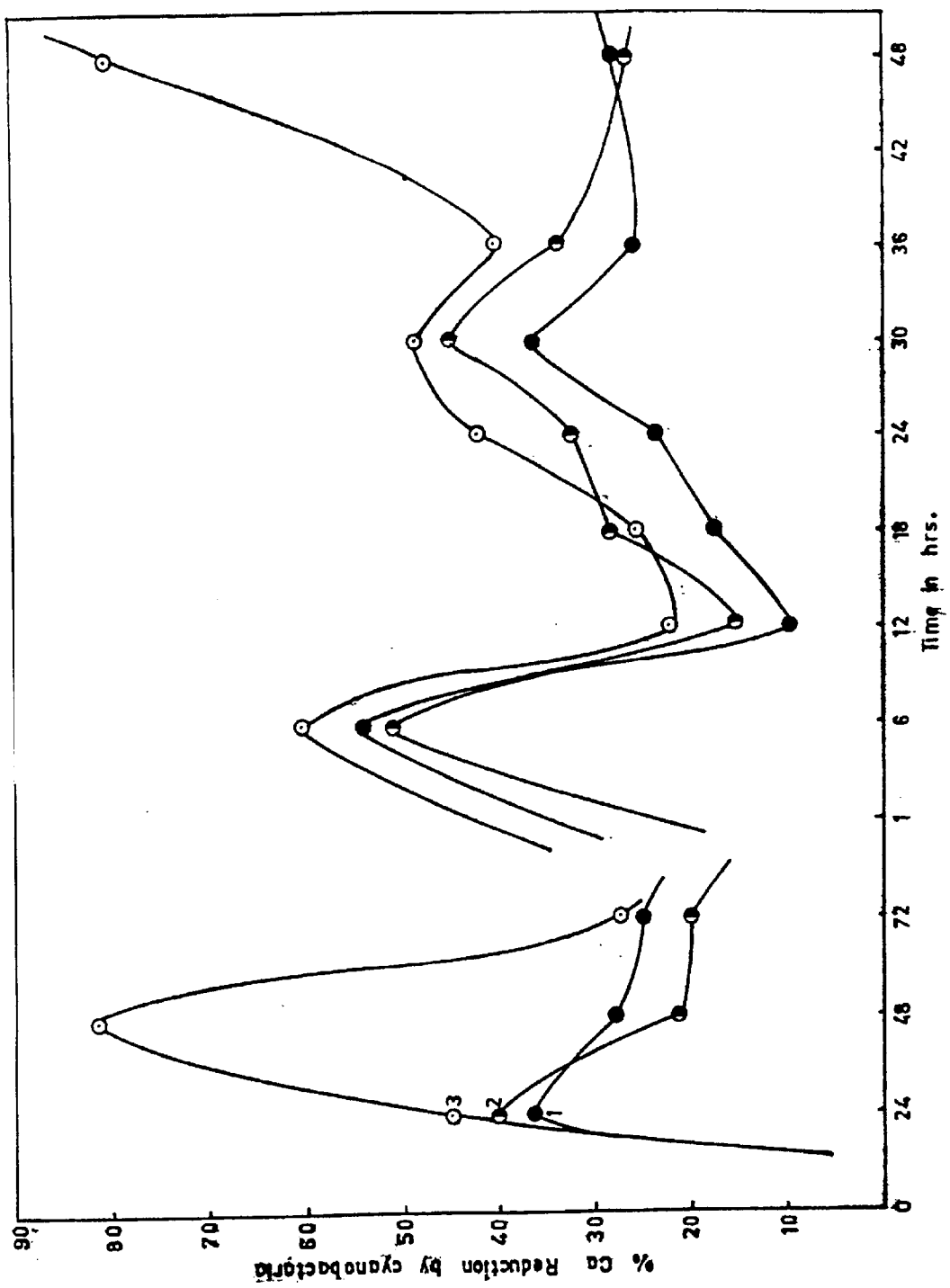

The present invention relates to an improved process for the removal of calcium ions from the brine by marine cyanobacteria.

The salt recovered from the brine in which the calcium is reduced has the applications (i) in chlor-alkali industry employing membrane cell or mercury cell technology for the manufacture of caustic soda and chlorine, (ii) in the manufacture of soda ash which has applications in preparation of many inorganic chemicals and detergents, (iii) in preparation of various other grades of high purity salt like, IP grade, AR grade, Dairy salt, etc., and (iv) in food industries as preservative where low calcium containing salt is desirable.

BACKGROUND OF THE INVENTION

Reference may be made to M. H. Vyas et al. (Indian Patent No. 315Del/95) wherein a method has been described for the preparation of sodium chloride containing low calcium impurity (Ca 0.16%) from sea brine using activated starch solution. Moreover the starch solution is heated prior to addition in sea brine solution. The limitation of this method is that the method is applicable to sea brine and not to subsoil brine. Besides, heating starch solution requires energy (power) which make the process uneconomical and unfeasible.

A. G. Bayer, in his paper "The importance of electrolyte quality to chlor-alkali cells, Unde Chlorine Symposium, 1995 has described the use of amino-phosphoric resin to remove calcium ions from the brine in the concentration range 4–10 g/L in presence of greater than 102 g/L of Sodium ions. The drawback associated with this process is the regeneration of resin; bringing it to the required cationic form; washing etc. makes the process more complicated, time-consuming and costly. Monitoring of this column involves additional manpower.

D. W. Kaufman in his book "Sodium chloride", Reinhold Publication Co., New York (1960), describes the use of (i) precipitants like calcium hydroxide and sodium carbonate to precipitate magnesium and calcium, and (ii) flocculent like poly-acrylamide to enhance the settling rate of the precipitates in the treatment of brine. The drawback of this process is that, the brine requires a prior chemical treatment to reduce the calcium and magnesium content. Moreover, the process also imbibes raises the problem of sludge disposal.

Z. Rant: Die Erzeugung von soda nach dem solvay verfahren, F. Enke-verlag, Stuttgart 1968 and H. Borger, Bergban Rundschau 4, 1952 described the purification of the brine which should be as near saturation as possible to achieve optimum sodium utilization, it is best carried out by the lime-soda process, which yields the precipitation of magnesium hydroxide and calcium as calcium carbonate. The reagents used in this precipitation are prepared by dissolving soda ash or milk of lime in brine ($Na_2CO_3$ concentration: 65–80 kg/m$^3$, $Ca(OH)_2$ concentration: 170–185 kg/m$^3$). Moreover, he has described that reaction times and settling rates are enhanced if the brine with the added reagent solution is mixed with recycled seed slurry. Under the described condition the precipitation of $Mg(OH)_2$ & $CaCO_3$ can be produced with settling rate upto 1 m/h and in some cases even 3 m/h. The drawback of the process is it needs chemicals for the precipitation of impurities like calcium and magnesium from the brine, which is costlier, and it also generates sludge and therefore disposal of the sludge creates environmental problems.

J. D. Adhiya et al., in Membrane Technology in Encyclopedia of Chemical Processes & Design, Marcel Dekker Inc., New York, Vol.29 (1988), in his paper, he said that International Salt Co., Salt Lake City, Utah, USA has described a mechanical method based on selectively heating (the resin bed on conveyor belt) and separating the salt and impurities in crushed rock salt. In this process, iron impurities are removed simultaneously by applying electromagnets. The drawbacks of the process are (i) an additional mechanical device is required to separate impurities from salt which adds to the cost of the product, (ii) besides, the separation is to be carried out at higher temperature; therefore energy (power) consumption increases. He has also disclosed the use of monovalent selective ion-exchange type membranes to concentrate the brine solution and remove the bivalent impurities viz. calcium, magnesium and sulphate. The concentrated brine solution is then subjected to evaporation process in order to crystallize salt with greater than 99.5% purity. The drawback of the process is, it needs a special preparation for monovalent selective membranes. The simultaneous removal of divalent cations and anions to prevent the clogging of membranes also needs special monitoring and washing.

A. I. Postornko et al. In U.S. Pat. No. 537,027-A (1976) has studied the dissolution kinetics of sodium chloride containing calcium sulphate as an impurity. In this process the flow rate and the contact time are so adjusted that highly soluble sodium chloride along with minor proportion of calcium sulphate is separated. The major proportion of calcium sulphate is recovered separately (undissolved). The drawback of the process is the accurate adjustment of flow rate and contact time is difficult which is to be maintained for a longer period. The disposal of sludge containing gypsum also involves an environmental problem.

R. F. Chambers et al. in U.S. Pat. No. 4,227,447-A (1981) and Toa GO Sci Chem. Ind. J. P. S7–106, 520-A2, K. Suzuki, R. Nagai, H. Goto (1982) has described the use of sodium bicarbonate or phosphoric acid in the treatment with saturated salt solution (brine) to reduce the calcium content. The author has revealed a recrystallization method for preparing pure salt from rock salt and sea salt. The process is based on solubility difference of sodium chloride and calcium carbonate at different temperatures. The author claims that under specified condition salt is soluble and insoluble calcium sulphate is removed by filtration. The filtered saturated salt solution is pumped to flash chamber where salt is crystallized. The drawback associated with this process is that the unit operation is increased which will eventually increase the time of completion of a specific batch. Besides, equal amount of investment is required, which would increase the capital investment. The process requires more energy (power).

D. Bayer, EZ709,728-C2 (R.Scharfer) (1983) and K. Maycock et al., SCI Chlorine Symposium, London (June, 1997) has described the calcium sulphate removal and K. Haycock et al., has removed calcium using ion exchange process or by membrane nanofiltration. The drawback of the process is it requires a huge plant, increasing investment and power.

A. U. Hamidani and J. R. Sanghavi, in their paper entitled "Improvement in the quality of salt from inland brine of Kharaghoda area", Salt Research & Industry, Vol.37, March 1992, India have explained the method of reducing the calcium content in sub-soil brine, by establishing a common ion effect in the saturated solution. The addition of $MgSO_4$ or $Na_2SO_4$ to the saturated solution in adequate amount creates a common ion effect and thereby the calcium sulphate is knocked out of the system. The drawback of the method is that by creating a common ion effect, calcium content is reduced, but the magnesium content is increased which is undesirable. The addition of $Na_2SO_4$ reduces the calcium but the sulphate content is increased which is also not desirable.

G. C. Jain et al., in their paper "Mixing of bitterns with weak brines in salt manufacture" in Salt Research & Industry, Vol.4, No.4, October 1967, India has described the process wherein the bittern is mixed with brine of less sodium chloride concentration in the condensers of the salt farms. In this mixing, due to the common ion effect the calcium sulphate is thrown out of the system. The drawback of the process is that it is difficult to accurately maintain the ratio of bittern to brine in the field, which does not give consistent result. Moreover the pumping of higher density bittern to weaker brine against the gravity results in higher content of Magnesium in salt which further needs large quantity of water to reduce Magnesium content, and incur higher washing loss.

Kaung-Hwa Yu et al., in their publication "A study on the collection of calcium from sea water using a recycling oleic acid system", in $8^{th}$ World Salt Symposium held at Netherlands, Vol.2, 2000 states that the use of oleic acid to remove calcium from sea-water as calcium-oleate. The concentrated calcium-oleate flocculates are decomposed into oleic acid and $CaCl_2$ by treating with HCl. The main drawback of the process is it adds many unit operations before recovery of low calcium salt. There could be the contamination of the precipitant and the precipitate generated in the process in the salt.

H. M. Patel, USA VIth Int. Sym. on Salt (1983) Vol. II, pp.515–533 has disclosed that using the difference in dissolution rate due to large difference in solubility between Sodium chloride and calcium sulphate the salt solution saturated with respect to sodium chloride, but with less calcium as calcium sulphate can be prepared. These differences in dissolution rates are important in designing the saturator. The process employs the unit operation like dissolver and chemical unit process reactor. It also requires addition of lime and soda for removal of magnesium and calcium, with this treatment and subsequent filtration of the brine. In view of these requirements in the process, the main drawback of this process is the increase in the capital investment and operating cost, which adversely affect the economy of the recovery of the low calcium salt.

In this method, the simple inventive steps adopted are (i) selecting specific type of cyanobacterial strains which has the affinity for calcium ions, (ii) the cyanobacteria after selection is used in very small amount, (iii) the cyanobacteria are effective in reducing calcium ions in brine solution with a very high salinity, (iv) the reduction of calcium ions by cyanobacteria is carried out at ambient temperature, (v) the cyanobacteria is self sustaining and the same can be reused for further removal of calcium from fresh brine, (vi) the process does not require any additional unit operation for separating adsorbed calcium ions.

OBJECTS OF THE INVENTION

An object of the present invention is to provide an improved process for the removal of calcium ions from brine using marine cyanobacteria, which obviates the drawbacks as detailed above.

Another objective of this present invention is to remove calcium ion impurity from concentrated brine in the density range 10–26° Be' using cyanobacteria at ambient conditions.

Yet, another objective of the present invention is to ascertain the cyclic behavior of calcium ions uptake and removal from the brine by marine cyanobacteria so that the same culture can be reused for the removal of calcium from the fresh brine.

Yet, another objective of the present invention is to provide an economical, simple and practical method for producing calcium free brine using marine cyanobacteria, without being subjected to the disadvantages and complexities involved in other known techniques.

SUMMARY OF THE INVENTION

To meet the above objects, the applicants developed a self-sustaining and cost effective process for the removal of calcium ions from the brine by using marine cyanobacteria at ambient temperature, which comprises the class of *Cyanophyceae* and family *Oscillatoriaceae*.

In this method, the simple inventive steps adopted are (i) selecting a specific type of cyanobacterial strains which have affinity for calcium ions, (ii) the cyanobacteria after selection are used in a very small amount, (iii) the cyanobacteria are effective in reducing calcium ions in brine solution with a very high salinity, (iv) the reduction of calcium ions by cyanobacteria is carried out at ambient temperature, (v) the cyanobacteria are self sustaining and the same can be reused for further removal of calcium from fresh brine, (vi) the process does not require any additional unit operation for separating adsorbed calcium ions.

DETAILED DESCRIPTION OF THE INVENTION

Accordingly, the present invention provides an improved process for the removal of calcium from brine by marine cyanobacteria, which comprises (i) culturing the marine cyanobacteria under known condition for a period of 42–48 hours to obtain young culture; (ii) inoculating the marine cyanobacteria so obtained to raw brine of 10 to 25.5oBe at ambient temperature; (iii) aging the mixture for a period of 3 to 96 hours in static condition at ambient temperature; ( v) maintaining the concentration of cyanobacteria in the range of 2 to 10 grams per liter (fresh weight) in sea brine/subsoil brine; (v) filtering the mixture to separate cyanobacteria and separately collecting the treated brine solution; (vi) adding the cyanobacteria so obtained to brine of low r density where it oozes the calcium to its maximum; (vii) re-inoculating the mixture so obtained as n (vi) at controlled rate to the fresh brine of higher density in order to further uptake/adsorb calcium and (viii) the self sustaining (autotrophic) property of cyanobacteria with euryhaline nature makes these cyanobacteria acclimatize and increase in biomass in severe brine condition without any external source of nutrients or energy.

It has been found that the improved process of the present invention, wherein a marine cyanobacteria is inoculated in sea brine and sub soil brine of 10 to 25.5o Baume (Be), is cost effective and practical method for producing calcium free brine. The marine cyanobacteria used do not require any external nutrients or energy. It is calcium from brine, which is one of the nutrient elements for the optimum growth, survival and biochemical activity. Thus, it increases in biomass. The uptake of calcium from brine is completed in about 3 hours to 24 hours and can give calcium reduction of about 70 percent. Such a brine (calcium content <0.022%) is useful intermediate in the preparation of high purity salt.

In an embodiment of the present invention, the marine cyanobacteria used for reducing the calcium in brine may be filamentous, oxygenic, halotolerant and must possess photosynthetic and Nitrogen-fixing properties.

In another embodiment of the present invention, the marine cyanobacteria used are, (1) *Lyngbya*, (2) *Oscillatoria*, (3) *Spirulina*, (4) *Anabaena*, (5) *Synechocystis*.

In yet another embodiment of the present invention, the sea-brine and sub-soil brine used contains total dissolved salts in the range of 1,10,000 to 2,30,000 ppm.

In yet another embodiment, the sea-brine and sub-soil brine used contains calcium in the range of 0.5 to 0.05 percent and density in the range of 10 to 25.5° Be'.

In yet another embodiment, the sea-brine and sub-soil brine used contains calcium in the range of 0.5 to 0.05 per cent.

In yet another embodiment, the density of the sea-brine and sub-soil brine is in the range of 10 to 25.5° Be'.

In still another embodiment of the present invention, the calcium removal from brine through biological means (by cyanobacteria) is cost effective and requires no external source of energy, chemical or nutrients.

In yet another embodiment of the present invention, the removal of calcium by cyanobacteria from brine is ecofriendly and does not generate/liberate any hazardous substance in the environment.

In still another embodiment of the present invention, the cyanobacteria were selected from a class of *Cyanophyceae* namely *Lyngbya, Oscillatoria, Sprulina, Anabaena* and *Synechocyssis*, which have affinity for calcium ions.

In still another embodiment of the present invention, the *cyanobaeteria* selected have a high salinity tolerance and can function most efficiently.

In still another embodiment of the present invention the selected *cyanobaeteria* are self-sustaining and therefore are recycled.

In accordance with the present invention it has been found that euryhaline marine cyanobacteria may be used to reduce the calcium content in the brine at ambient conditions. *Cyanobacteria* are photosynthetic prokaryote having nitrogen-fixing capability, their halo tolerance and other stress tolerance phenomena are dependent on calcium ions. The Photosynthetic System-II (PS-II) activity also depends on the concentration of calcium in the medium for its growth. The trichomes of this filamentous marine *Cyanobacteria* are motile an calcium plays an essential role in the motility of the *Cyanobacteria*. An increase in the inorganic phosphate has been reported by addition of calcium in the cultures of *Cyanobacteria*. There are number of processes in *Cyanobacteria* which are calcium mediated, e.g. sporulation, akinete formation, heterocyst differentiation (frequency), nitrogen fixation, etc. The activation of photosyntheti active centres by calcium suggests a mechanism by which cyanobacteria may enhance photosynthesis to offset decreased photon flux; the enhancement of nitrogen fixation by calcium, through protection of the O2 labile nitrogenous, could act against the effects of O2. In summary there is much to be said and investigated in support of the hypothesis for calcium mediated regulation of physiological processes in cyanobacteria and as yet no substantial evidence against the concept is existing.

The mechanism for the calcium uptake by the marine cyanobacteria employed in this process of removal of calcium from the brine of varying densities and different ionic composition lies in the essential requirement of divalent ions by the enzymes for its either protection or activity needed in the metabolism. The role of calcium as a second messenger and calmodulin, a signal transducer protein in the osmoregulation (Halotolerance phenomena) is very vital in this process. Another indispensable role of calcium ions is protecting the oxygen sensitive enzymes like nitrogenase (for the Nitrogen-fixation). Hence, calcium is an essential nutrient element for the optimum growth, survival (under stress) and their biochemical activity. And in this particular process the necessity of cyanobacteria for the divalent calcium has become the mother of invention which is required for the brine purification by removing the impurity leading to the better quality and quantity of the salt produced through solar evaporation and sea brine and subsoil brine.

The marine cyanobacteria was exploited with an innovative idea of improving the process of brine purification (in situ) by removing the calcium impurity through biological means which is cost effective and requiring no external source of energy, chemical or labor. There were series of innovative steps carried out to develop this eco-friendly technology which does not liberate or produce any hazardous substance in the environment rather the extra bio-mass produced can be used as an aqua feed (by-product). The euryhaline species of cyanobacteria selected which has a wide range (10–26° Be') of salinity tolerance as they can survive and function efficiently and due to its self-sustaining nature they could be reused, so it is recyclable too. After establishing the cyclic trend of cyanobacteria in calcium uptake (in 48 hrs) and removal (in 48–72 hrs) and then repeated behavior, the same biomass of cyanobacterial culture could be used after oozing of calcium is over (in diluted brine) for the removal of calcium in the fresh brine of higher density. All these physiological functions takes place under the ambient conditions and the sea brine as well as subsoil brine itself acts as its medium for growth, hence no extra-nutrient is needed and because they are photosynthetic and Nitrogen-fixing they are capable of building their own food (organic) themselves.

The unique biochemical properties of cyanobacteria in leaching the calcium without any extra effort provides them an ecological niche for future field trials in salt farms at critical and most difficult stages where no other chemical process can function i.e. in the polishing of brine by removing the last traces of calcium impurity in order to yield the best quality salt for the industry.

DETAILED DESCRIPTION OF THE ACCOMPANYING DRAWINGS

The FIG. 1 represents the cyclic trend of cyanobacterial strains (*Anabaena*-1; *Oscillatoria*-2 and *Lyngbya*-3) for calcium removal in sea/sub-soil brine.

The following examples are given by way of illustration and therefore should not be construed to limit the scope of the present invention.

EXAMPLE-1

A known volume (500 ml) of sea brine collected from the coast of Bhavnagar District, Gujarat, India, which had a density of 11.5° Be', calcium content of 0.0603% and a total dissolved solids of 1,20,000 ppm was taken in a cotton plugged conical flask. This brine was inoculated with 4.0 gms of fresh *Spirulina* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-2

A known volume (500 ml) of sea brine collected from the coast of Bhavnagar District, Gujarat, India, which had a density of 11.5° Be', calcium content of 0.0603% and a total dissolved solids of 1,20,000 ppm was taken in a cotton plugged conical flask. This brine was inoculated with 4.0 gms of fresh *Lyngbya* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-3

A known volume (500 ml) of sea brine collected from the coast of Bhavnagar District, Gujarat, India, which had a density of 11.5° Be', calcium content of 0.0603% and a total dissolved solids of 1,20,000 ppm was taken in a cotton plugged conical flask. This brine was inoculated with 4.0 gms of fresh *Anabaena* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-4

A known volume (500 ml) of sea brine collected from the coast of Bhavnagar District, Gujarat, India, which had a density of 11.5° Be', calcium content of 0.0603% and a total dissolved solids of 1,20,000 ppm was taken in a cotton plugged conical flask. This brine was inoculated with 4.0 gms of fresh *Synechocystis* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-5

A known volume (500 ml) of sea brine collected from the coast of Bhavnagar District, Gujarat, India, which had a density of 11.5° Be', calcium content of 0.0603% and a total dissolved solids of 1,20,000 ppm was taken in a cotton plugged conical flask. This brine was inoculated with 4.0 gms of fresh *Oscillatoria* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-6

A known volume (500 ml) of sea brine collected from the coast of Bhavnagar District, Gujarat, India, which had a density of 11.5° Be', calcium content of 0.0603% and a total dissolved solids of 1,20,000 ppm was taken in a cotton plugged conical flask. This brine was inoculated with 4.0 gms of fresh Consortium (cyanobacteria) and kept in static condition for 24 hours at 30° C. temperature. After the stipulated time, 50 ml of brine was withdrawn, filtered completely free from cyanobacteria and the calcium content was estimated by complexometric titration. The reduction of calcium in percentage, from 11.5° and 24.0° Baume of sea-brine using different cyanobacteria is shown in Table-1.

TABLE 1

| | | Sea Brine | | | | | |
| --- | --- | --- | --- | --- | --- | --- | --- |
| | | 11.5° Be' $Ca^{++}$ Conc. (0.06031%) | | | 24.0° Be' $Ca^{++}$ Conc. (0.3920%) | | |
| Cyanobacteria (5 g/l) | Contact time (hrs) | Present | Removed | % removal | Present | Removed | % removal |
| Spirulina | 24 | 0.039 | 0.021 | 35.06 | — | — | — |
| Lyngbya | 24 | 0.033 | 0.027 | 44.79 | 0.245 | 0.146 | 37.42 |
| Anabaena | 24 | 0.033 | 0.020 | 39.92 | 0.309 | 0.082 | 20.94 |
| Synechocystis | 24 | 0.032 | 0.027 | 45.70 | — | — | — |
| Oscillatoria | 24 | 0.032 | 0.020 | 34.62 | 0.292 | 0.099 | 25.36 |
| Consortium | 24 | 0.038 | 0.021 | 34.62 | — | — | — |

EXAMPLE-7

A known volume (500 ml) of subsoil brine collected from the coast of Bhavnagar District, Gujarat, India, which had a density of 13.0° Be', calcium content of 0.282% and a total dissolved solids of 1,20,000 ppm was taken in a cotton plugged conical flask. This brine was inoculated with 4.0 gms of fresh *Spirulina* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-8

A known volume (500 ml) of subsoil brine collected from the coast of Bhavnagar District, Gujarat, India, which had a density of 13.0° Be', calcium content of 0.282% and a total dissolved solids of 1,20,000 ppm was taken in a cotton plugged conical flask. This brine was inoculated with 4.0 gms of fresh *Lyngbya* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-9

A known volume (500 ml) of subsoil brine collected from the coast of Bhavnagar District, Gujarat, India, which had a density of 13.0° Be', calcium content of 0.282% and a total dissolved solids of 1,20,000 ppm was taken in a cotton plugged conical flask. This brine was inoculated with 4.0 gms of fresh *Anabaena* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-10

A known volume (500 ml) of subsoil brine collected from the coast of Bhavnagar District, Gujarat, India, which had a density of 13.0° Be', calcium content of 0.282% and a total dissolved solids of 1,20,000 ppm was taken in a cotton plugged conical flask. This brine was inoculated with 4.0 gms of fresh *Synechocystis* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-11

A known volume (500 ml) of subsoil brine collected from the coast of Bhavnagar District, Gujarat, India, which had a density of 13.0° Be', calcium content of 0.282% and a total dissolved solids of 1,20,000 ppm was taken in a cotton plugged conical flask. This brine was inoculated with 4.0 gms of fresh *Oscillatoria* (cyanobacteria) and kept in static condition for 24 hours at 30° C. temperature. After the stipulated time, 50 ml of brine was withdrawn, filtered completely free from cyanobacteria and the calcium content was estimated by complexometric titration.

EXAMPLE-12

A known volume (500 ml) of subsoil brine collected from the coast of Bhavnagar District, Gujarat, India, which had a density of 13.0° Be', calcium content of 0.282% and a total dissolved solids of 1,20,000 ppm was taken in a cotton plugged conical flask. This brine was inoculated with 4.0 gms of fresh *Consortium* (cyanobacteria) and kept in static condition for 24 hours at 30° C. temperature. After the stipulated time, 50 ml of brine was withdrawn, filtered completely free from cyanobacteria and the calcium content was estimated by complexometric titration. The reduction of calcium in percentage from 13.0° and 24.0° Baume of subsoil brine using different cyanobacteria is shown in Table-2.

5. The cyclic behavior of the cyanobacteria for uptake and oozing of calcium from the brine. Due to this behavior, the same cyanobacterial culture can be reused for the same purpose or it can be used as an aqua feed (byproduct).
6. The marine cyanobacteria used in this process is isolated from our own sea coast of Arabian sea in the southwest region, hence it is halotolerent species with better metabolism having wide range of stress tolerance leading to better efficiency.

*Lyngbya aesturaii* SM-1 was deposited with ATCC on August 19, 2002 under Patent Deposit Designation PTA-4602, and *Consortium* was deposited with ATCC on August 19, 2002 under Patent Deposit Designation PTA-4603.

What is claimed is:

1. A method for production of salt from sea brine or subsoil brine with reduced calcium ion impurities, by removing calcium from the sea brine or subsoil brine, comprising (i) isolating marine cyanobacteria in pure form am hyper-saline habitat and culturing the isolated marine cyanobacteria in brine, (ii) inoculating the resultant cyanobacterial culture to concentrated raw brine for uptake of calcium ions, (iii) removing the cyanobacteria from the raw brine and immersing the cyanobacteria in dilute brine to ooze out accumulated calcium in the resultant cyanobacterial mass, (iv) recycling the cyan bacteria in a fresh batch of concentrated raw brine, (v) evaporating the treated raw brine up to a density of 25.5° Be', (vi) charging the resultant brine into a crystallizer and allowing salt to be produced up to a density of 29° Be', wherein removal of calcium ions by cyanobacteria results in salt having reduced calcium ion impurities.

2. The method as claimed in claim 1, wherein the marine cyanobacteria are isolated from hyper-saline environments in the west sea coast of India, and belong to the class of *Cyanophyceae*.

TABLE 2

| | | Sub-soil Brine | | | | |
| --- | --- | --- | --- | --- | --- | --- |
| | | 13.0° Be' Initial Ca: 0.282% | | | 24.0° Be' Initial Ca: 0.388% | |
| Cyanobacteria (5 g/L) | Contact time (hrs) | Present | Removed | % removal | Present | Removed | % removal |
| Spirulina | 24 | 0.194 | 0.088 | 31.31 | — | — | — |
| Lyngbya | 24 | 0.177 | 0.104 | 37.09 | 0.205 | 0.182 | 46.96 |
| Anabaena | 24 | 0.176 | 0.106 | 37.32 | 0.251 | 0.137 | 35.31 |
| Synechocystis | 24 | 0.162 | 0.119 | 42.45 | 0.214 | 0.174 | 44.85 |
| Oscillatoria | 24 | 0.180 | 0.101 | 36.12 | 0.230 | 0.158 | 40.72 |
| Consortium | 24 | 0.183 | 0.098 | 35.11 | — | — | — |

The main advantages of the present invention are:
1. The advantage of this invention is the flexibility and versatility showed by the marine cyanobacteria in calcium leaching process with a greater efficiency showing 60–80% reduction in calcium impurity which will result in much better quality salt.
2. This process does not require any extra chemical energy or labor and it works under natural condition.
3. The ecological balance is maintained i.e. it is ecofriendly process.
4. When sulphate is more calcium can be more easily removed as calcium sulphate from sea brine. However, when sulphate is less (in subsoil brine), calcium removal is more difficult.

3. The method as claimed in claim 1, wherein the marine cyanobacteria are from the family of *Oscillatoriaceae*.

4. The method as claimed in claim 1, wherein the marine cyanobacteria are selected from the group consisting of *Lyngbya aestuarii* SM-1, *Oscillatoria* sp., *Spirulina* sp., *Anabaena* sp. and *Synechocystis* sp.

5. The method as claimed in claim 4, wherein the marine cyanobacteria are selected from the group consisting of (1) *Lyngbya aestuarii* SM-1 (ATCC PTA-4602) and (2) the *Consortium* ATCC PTA-4603.

6. The method as claimed in any one of claims 1–3, wherein the marine cyanobacteria are cultured either singly or in the form of a consortium.

7. The method as claimed in any on of claims 1–3, wherein the marine cyanobacteria are isolated in pure form using a serial dilution method.

8. The method as claimed in claim 7, wherein the isolated marine cyanobacteria are cultured in brine without any added nutrients.

9. The method as claimed in claim 8 wherein the isolated marine cyanobacteria are cultured in brine of 3–16° Be' density for a period of 36–72 hours.

10. The method as claimed in claim 1, wherein the brine resulting from (ii) has a density in the range of 18–25° Be' and a major portion of calcium ions impurity in the brine is converted to gypsum ($CaSO_4.2H_2O$) during concentration of the brine beyond 14° Be', thereby minimizing the load on the marine cyanobacteria and simultaneously minimizing the volume of brine.

11. The method as claimed in claim 10, wherein the brine resulting from (ii) has a density of 20–24° Be'.

12. The method as claimed in claim 1, wherein the fresh wet weight of cyanobacteria inoculated into the raw concentrated brine is in the rang of 1–10 g/L.

13. The method as claimed in claim 12, wherein the cyanobacteria is in contact with the raw concentrated brine for a contact time of 6–48 hours.

14. The method as claimed in claim 1, wherein the cyanobacteria removes 1–100% of calcium ions in the concentrated raw brine.

15. The method as claimed in claim 14 wherein 30–70% of calcium ions is removed.

16. The method as claimed in claim 1, wherein in (ii) the cyanobacteria are exposed to the concentrated raw brine for a time effective to remove calcium ions from the concentrated raw brine, and in (iii) the cyanobacteria are exposed to dilute brine of density in the range of 3–15° Be' for time effective to remove the accumulated calcium ions from the resultant cyanobacterial mass before the cyanobacteria are recycled into a fresh batch of concentrated raw brine.

17. The method as claimed in claim 16, wherein exposure to the dilute brine is conducted for 1–2 hours.

18. The method as claimed in claim 1, that is implemented in solar salt works.

* * * * *